(12) United States Patent
Macdonald et al.

(10) Patent No.: US 11,000,293 B2
(45) Date of Patent: May 11, 2021

(54) AUTOCLAVE TOLERANT BATTERY POWERED MOTORIZED SURGICAL HAND PIECE TOOL AND MOTOR CONTROL METHOD

(71) Applicant: Conmed Corporation, Utica, NY (US)

(72) Inventors: Alistair M. Macdonald, Oldsmar, FL (US); John K. Sieh, Safety Harbor, FL (US); Michael J. DeCesare, New Port Richey, FL (US); Richard E. Kienman, Tampa, FL (US); David Gonzalez, Apollo Beach, FL (US); Richard Medero, Apollo Beach, FL (US)

(73) Assignee: Conmed Corporation, Utica, NY (US)

( * ) Notice: Subject to any disclaimer, the term of this patent is extended or adjusted under 35 U.S.C. 154(b) by 899 days.

(21) Appl. No.: 15/088,882

(22) Filed: Apr. 1, 2016

(65) Prior Publication Data

US 2016/0287265 A1   Oct. 6, 2016

Related U.S. Application Data

(60) Provisional application No. 62/142,595, filed on Apr. 3, 2015.

(51) Int. Cl.
*A61B 17/16* (2006.01)
*A61B 17/14* (2006.01)
(Continued)

(52) U.S. Cl.
CPC .......... *A61B 17/1628* (2013.01); *A61B 17/14* (2013.01); *A61B 90/08* (2016.02);
(Continued)

(58) Field of Classification Search
CPC combination set(s) only.
See application file for complete search history.

(56) References Cited

U.S. PATENT DOCUMENTS 5,426,428 A  *  6/1995  Binder ...................... A61L 2/07
                                                 340/870.01
5,792,573 A       8/1998  Pitzen et al.
(Continued)

FOREIGN PATENT DOCUMENTS

CN        102868350        1/2013
CN        103762913        4/2014
(Continued)

OTHER PUBLICATIONS

International Search Report and Written Opinion Form PCT/ISA/220, International Application No. PCT/US2016/025623, p. 1-23, dated Aug. 18, 2016.
(Continued)

*Primary Examiner* — Scott Luan
(74) *Attorney, Agent, or Firm* — Bond, Schoeneck & King, PLLC; Frederick J. M. Price

(57) ABSTRACT

A single cell power unit for a motorized surgical power tool includes a single cell power unit enclosure. A high temperature battery cell is mechanically supported within and disposed at about a center of the single cell power unit enclosure. An electrical connector having a plurality of connector pins is configured to couple to a mating electrical connector of a tool part having a motor. A motorized surgical handpiece tool which prevents the motor from operating when the power unit is removed, a method to start a multi-phase brushless sensorless motor of a surgical hand piece tool in a controlled manner, a power unit for a motorized surgical power tool with a battery insulated by a flexible circuit boards, and a safety switch system for a motorized surgical power tool with a lever magnet motor speed control are also described.

14 Claims, 16 Drawing Sheets

(51) Int. Cl.

| | | |
|---|---|---|
| *H01M 10/39* | (2006.01) | |
| *H01M 10/0525* | (2010.01) | |
| *H01M 10/04* | (2006.01) | |
| *A61B 90/00* | (2016.01) | |
| *H05K 7/14* | (2006.01) | |
| *H01M 2/10* | (2006.01) | |
| *H01M 10/658* | (2014.01) | |
| *H01M 10/052* | (2010.01) | |
| *H02P 6/20* | (2016.01) | |
| *H01M 10/6235* | (2014.01) | |
| *H01M 10/42* | (2006.01) | |
| *H02P 6/21* | (2016.01) | |
| *H02P 6/182* | (2016.01) | |
| *H05K 1/18* | (2006.01) | |
| *A61B 17/00* | (2006.01) | |
| *H05K 1/02* | (2006.01) | |

(52) U.S. Cl.
CPC ....... *H01M 2/1022* (2013.01); *H01M 2/1094* (2013.01); *H01M 10/0436* (2013.01); *H01M 10/052* (2013.01); *H01M 10/0525* (2013.01); *H01M 10/39* (2013.01); *H01M 10/4257* (2013.01); *H01M 10/6235* (2015.04); *H01M 10/658* (2015.04); *H02P 6/182* (2013.01); *H02P 6/20* (2013.01); *H02P 6/21* (2016.02); *H05K 1/18* (2013.01); *H05K 7/1432* (2013.01); *A61B 2017/00017* (2013.01); *A61B 2017/0046* (2013.01); *A61B 2017/00115* (2013.01); *A61B 2017/00221* (2013.01); *A61B 2017/00734* (2013.01); *A61B 2017/00876* (2013.01); *A61B 2090/0813* (2016.02); *H01M 2010/4278* (2013.01); *H01M 2220/30* (2013.01); *H05K 1/0201* (2013.01); *H05K 1/0262* (2013.01); *H05K 2201/0397* (2013.01); *H05K 2201/10037* (2013.01)

(56) References Cited

U.S. PATENT DOCUMENTS

| | | |
|---|---|---|
| 7,209,784 B2 | 4/2007 | Schmidt |
| 7,501,198 B2 | 3/2009 | Barlev et al. |
| 8,486,560 B2 | 7/2013 | Tartaglia |
| 2004/0092992 A1 | 5/2004 | Adams et al. |
| 2007/0090788 A1 | 4/2007 | Hansford et al. |
| 2015/0157354 A1* | 6/2015 | Bales, Jr. ............ B06B 1/0223 606/169 |

FOREIGN PATENT DOCUMENTS

| | | |
|---|---|---|
| CN | 103997268 | 8/2014 |
| EP | 1029385 | 8/2000 |
| EP | 2510891 | 10/2012 |
| GB | 2408396 | 5/2005 |
| JP | 2006116041 | 5/2006 |

OTHER PUBLICATIONS

Infineon Technologies AG, AP08018, EX 866—Start-up Control Algorithm for Sensorless and Variable Load BLDC Control Using Variable Inductance Sensing Method, Application Noe, V1.0, Oct. 2006.

Linear Technology, LTC 1502-3.3; Single Cell to 3.3V Regulated Charge Pump DC/DC Converter.

European Search Report, EPO Form 1503, EP Application No. 20 17 3280, pp. 1-10, dated Jul. 30, 2020.

* cited by examiner

AUTOCLAVE TOLERANT BATTERY POWERED MOTORIZED SURGICAL HAND PIECE TOOL AND MOTOR CONTROL METHOD

CROSS-REFERENCE TO RELATED APPLICATIONS

This application claims priority to U.S. Provisional Patent Application Ser. No. 62/142,595 filed on Apr. 3, 2015 and entitled "Autoclave Tolerant Single Cell Motorized Surgical Hand Piece Tool and Motor Control Method" the entire disclosure of which is incorporated herein by reference.

FIELD OF THE APPLICATION

The application relates to surgical tools and more particularly to battery operated motorized surgical tools.

BACKGROUND

Motorized surgical tools including battery operated tools are well known in the art. In order to develop the needed motor power, such as for a portable surgical saw, conventional motorized surgical tools generally use a plurality of batteries wired in series and or parallel. However, the inclusion of several batteries greatly increases the weight of the device, making it difficult to hold and to precisely maneuver during surgical procedures. Accordingly, there exists a need in the art for a surgical device having a single battery (or multiple smaller batteries) that is relatively lightweight such that it is easy to maneuver during surgical procedures.

Another problem with conventional rechargeable battery powered surgical instruments is that the battery packs need to be sterilized between medical procedures through the autoclaving process. Conventional multiple lithium ion cell battery packs need to be treated with some care so as not damage the battery pack during sterilization. In some cases, only low temperature sterilization can be used, typically by chemical sterilization, such as by exposing the pack to a peroxide gas plasma. In other cases, multiple cell battery packs can be placed in an autoclave, however only for a very short period of time (e.g. under four minutes exposure) and at limited dry times and temperatures. By contrast, some medical sterilization protocols have a minimum 18 minute high temperature exposure requirement followed by a 45 minute heated drying time autoclave cycle—preventing conventional battery packs from meeting necessary sterilization protocols. Also, many autoclave systems use a series of temperature and pressure cycles including several periods of high temperature and vacuum pressure that battery packs were not designed to withstand. Accordingly, there exists a need in the art for a power unit that can withstand the autoclave process.

In conventional designs of handheld surgical devices that utilize pins to provide an electrical connection between electronic circuits, which need to be protected and sealed away from the extreme environment of the autoclave, the pins were either over molded or potted. However, each pin provides a potential path for the high pressure steam from the autoclave to enter the enclosure, therefore reducing the number of pins will improve reliability by reducing the number of potential leak paths, as described below in the detailed description. Accordingly, a need exists in the art to reduce the number of pins that must be sealed and that provide a potential path for high pressure steam.

Motors in surgical tools must also be able to turn in a carefully controlled and predictable manner in response to movements of a motor speed control lever by the surgeon. Adding to the complexity of the starting process is that the torque loading can range from towards binding if the cutting edge of the tool bit is, for example, against a bone, to virtually no torque loading if the bit or saw blade is in air and not yet held against the surface to be cut. Some conventional surgical tools apply a nominal starting sequence which works well on average. However, such starting can be rough and also can cause a jerking motion of the tool and/or the tool bit. Accordingly, there exists a need in the art for a method to smoothly start the motor without an accompanying jerking motion of the tool or toolbit.

The maximum speed of a motor is determined by the voltage applied across its terminals. If it is being powered by a battery using a lead acid or nickel technology, the decline of the battery voltage is discernible almost straight from the point of full charge. One of the advantages of lithium technology batteries is that they maintain their voltage much better, until the last few percent of remaining charge. A motor-driving application with electronic speed control will further compensate for a falling voltage by adjusting the length of the motor control pulses. Often, the first inkling the user has that the charge is depleted is that the motor suddenly stops. This could be extremely inconvenient if this event were to occur in the middle of a delicate maneuver during a procedure.

A visual warning indicator e.g. fuel gauge, flashing LED, is problematic as it may well be obscured due to the way of holding the handpiece, or the surgeon concentrating entirely on his work. An audio sensor is a possibility, although there are severe constraints on space, sound transmission through a battery case, and lack of transducers with suitable temperature characteristics. The motor itself can be made to sound, but this can only work while the motor is stationary, and would therefore interrupt the procedure. With the relatively poor start-up characteristics of a sensorless motor, there is also a risk of inability to restart after. Accordingly, there exists a need to notify the user of a low battery without relying on a visual or auditory indicator.

SUMMARY

According to an aspect, a power unit for a motorized surgical tool comprises: an outer enclosure defining an interior cavity; a single battery cell fully disposed within said interior cavity; and a printed circuit board disposed within said interior cavity.

According to an embodiment, the power unit further comprises at least one layer of insulation at least partially wrapped around said at least one battery as a layer of thermal insulation.

According to an embodiment, the printed circuit board is at least partially formed from a flexible printed circuit board material.

According to an embodiment, the battery cell is a high-temperature battery.

According to an embodiment, the power unit further comprising a hermetic connector extending from the enclosure, wherein the enclosure and hermetic connector are together hermetically sealed.

According to an embodiment, a bulkhead surrounding the hermetic connector further comprises an O-ring configured as a radial seal and stretched into a non-circular path to seal a junction between the bulkhead and the enclosure.

According to an embodiment, the hermetic connector further comprises a plurality of pins.

According to an embodiment, at least one of the plurality of pins is a hyperbolic pin socket.

According to an embodiment, at least one of the plurality of pins is in communication with the printed circuit board, wherein the printed circuit board is configured to multiplex a first signal and a second signal over the at least one pin of the plurality of pins.

According to an embodiment, the interior cavity of the enclosure is a vacuum.

According to an embodiment, the power unit further comprises a one-way check valve in communication with the interior cavity and an exterior surface of the enclosure, wherein the one-way check valve is configured to refresh the vacuum of the enclosure when the exterior surface of the enclosure is exposed to a vacuum.

According to an embodiment, the power unit further comprises a canted spring disposed in a channel to secure said power unit to a surgical handpiece motorized unit.

According to an embodiment, the power unit further comprises a transceiver configured to communicate with a computing device.

According to an embodiment, the power unit is configured to vary the power delivered to a surgical handpiece motorized unit having a motor, such that the speed of the motor may vary in a predetermined way that is perceptible to a user.

According to another aspect, a method for starting brushless direct current motor, comprises the steps of: providing a brushless direct current motor having a rotor configured to rotate in at least one direction and a having stator comprising a plurality of phases, wherein, for any given position of the rotor, at least two combinations of the plurality of phases are positioned to, when powered, induce the rotor to rotate; applying a voltage to at least a first phase combination of a plurality of phases and a second phase combination of the plurality of phases, wherein both of the first phase combination and the second phase combination induce the rotor to rotate in the first direction when powered; comparing a first current drawn by the first phase combination and a second current drawn by the second phase combination; and applying a voltage to at least a third phase combination of the plurality of phases and the second phase combination of the plurality of phases upon determining that the current drawn by the second phase combination is less than the current drawn by the first phase combination.

According to an embodiment, the first phase combination and second phase combination are selected from the plurality of phases according to an initial position of the rotor.

According to an embodiment, the initial position of the rotor is determined by measuring the current drawn by a plurality of phase combinations of the plurality of phases, in response to a voltage applied to each of the plurality of phase combinations.

According to an embodiment, the current drawn by the first phase combination and the second phase combination is measured according to the voltage drop across a shunt resistor.

According to an aspect, a motorized surgical tool comprises: a power unit comprising a battery and first connector and a sensor; a motorized unit having a motor; a lever arm mounted to said motorized unit by a pivot point, wherein a magnet, having a magnetic field, is disposed upon the lever arm and positioned such that pressing the lever arm will alter a distance between the magnet and the sensor, wherein the sensor is configured to detect a strength of the magnetic field, wherein the power unit is configured to deliver power to the motorized unit according to the sensed strength of the magnetic field.

According to an embodiment, the power unit further comprises a first connector, and the motorized unit further comprises second connector, wherein the second connector is configured to mate with the first connector such that the power unit is detachable from the motorized unit by separating the second connector from the first connector, wherein the magnet is sized and positioned on the lever, such that separating the second connector from the first connector will not alter the sensed strength of the magnetic field by the sensor, until the second connector is fully separated from the first connector.

According to an aspect, a power unit for a motorized surgical tool comprises: an outer enclosure defining an interior cavity; at least one battery cell fully disposed within said interior cavity; and a printed circuit board disposed within said interior cavity and at least partially wrapped around said at least one battery cell as a layer of thermal insulation.

According to an aspect, a power unit for a motorized surgical tool, comprises: an outer enclosure defining an interior cavity; a single battery cell fully disposed within said interior cavity; and a printed circuit board disposed within said interior cavity.

According to an embodiment, the printed circuit board further comprises a boost converter configured to step up a voltage supplied by the single battery cell.

According to an embodiment, the single battery cell has a low internal impedance.

According to an embodiment, the single battery cell is comprised of a Lithium ion ceramic cell.

According to an embodiment, the voltage is stepped up to 10 V.

According to an embodiment, the single cell battery supplies 22 A of current.

According to an embodiment, the single cell battery is directly attached to the printed circuit board, such that ripples in a voltage supplied by the single cell battery are mitigated.

According to an embodiment, the single cell battery is attached to the printed circuit board by a pair of tabs, wherein the tabs are sized and dimensioned such that ripples in a voltage supplied by the single cell battery are mitigated.

According to an aspect, a method for a notifying a user of a handheld surgical device, comprises: measuring a first metric, having a first value; comparing the first value to a predetermined value; changing a velocity of a motor from a first velocity to a second velocity, such that the change is perceptible to a user.

According to an embodiment, the first velocity is lower than the second velocity.

According to an embodiment, the second velocity is lower than the first velocity.

According to an embodiment, the motor changes to the second velocity after a predetermined period of time.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

DETAILED DESCRIPTION

Figure 1:
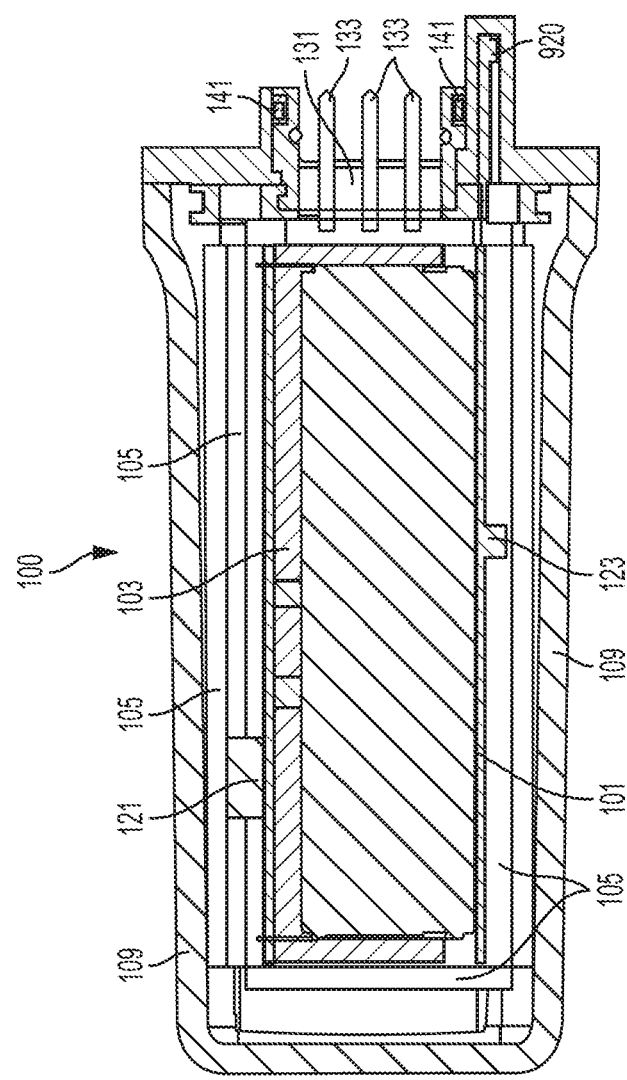
FIG. 1 shows a section view of an exemplary embodiment of a power unit, according to an embodiment.
Figure 2:
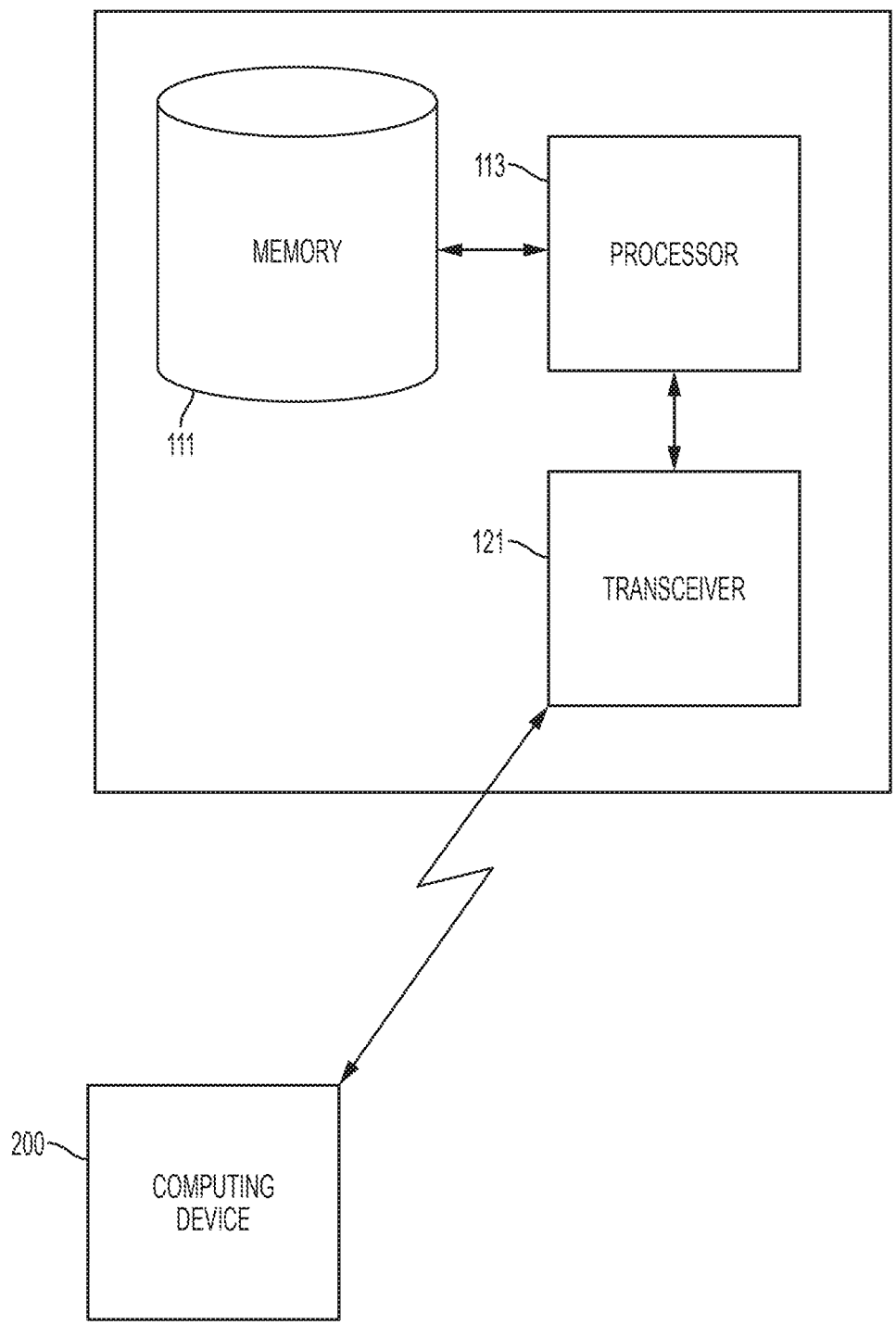
FIG. 2 shows a schematic of a device, according to an embodiment.

Referring to the figures, there is shown in FIG. 1 an embodiment of an autoclave-tolerant power unit 100 for powering, among other things, a surgical tool. Power unit 100 may comprise a battery 101, a printed circuit board 103, insulation 105, and a power unit enclosure 109. In an embodiment, enclosure 109 is hermetically sealed to protect battery 101 and printed circuit board 103 during the autoclave process. In an embodiment, printed circuit board 103 may include (as shown in FIG. 2) a non-transitory storage medium (i.e. memory) configured to store a plurality of program instructions, and a processor configured to execute the program instructions stored in the memory. Further, printed circuit board 103 may be configured to control battery management functions and motor control (of an attached or otherwise included motor), as well as other operations and features described in this disclosure.

Power unit 100 may further comprise connector 131, including a plurality of pins 133, extending out of the unit enclosure 109 and configured for, at least, delivering power from battery 101 to an attached motor (or other implement), such as described in conjunction with FIG. 9 below. Power unit 100 may further include a one-way check valve 141 to refresh the vacuum during the autoclave process.

As shown in FIG. 1, in an embodiment, power unit 100 may be structured in a multi-tiered configuration to provide thermal insulation to battery 101 during the autoclave process. In an embodiment, the multi-tiered configuration may include printed circuit board 103, insulation 105, and enclosure 109 each disposed in at least a partial covering relation with battery 101, such that printed circuit board 103, insulation 105, and enclosure 109 each serve to, in part, thermally insulate battery 101. Furthermore, in an embodiment, battery 101 may be fully enclosed by each layer. In an alternate embodiment, printed circuit board 103 and/or insulation 105 may each partially enclose battery 101.

Figure 1A:
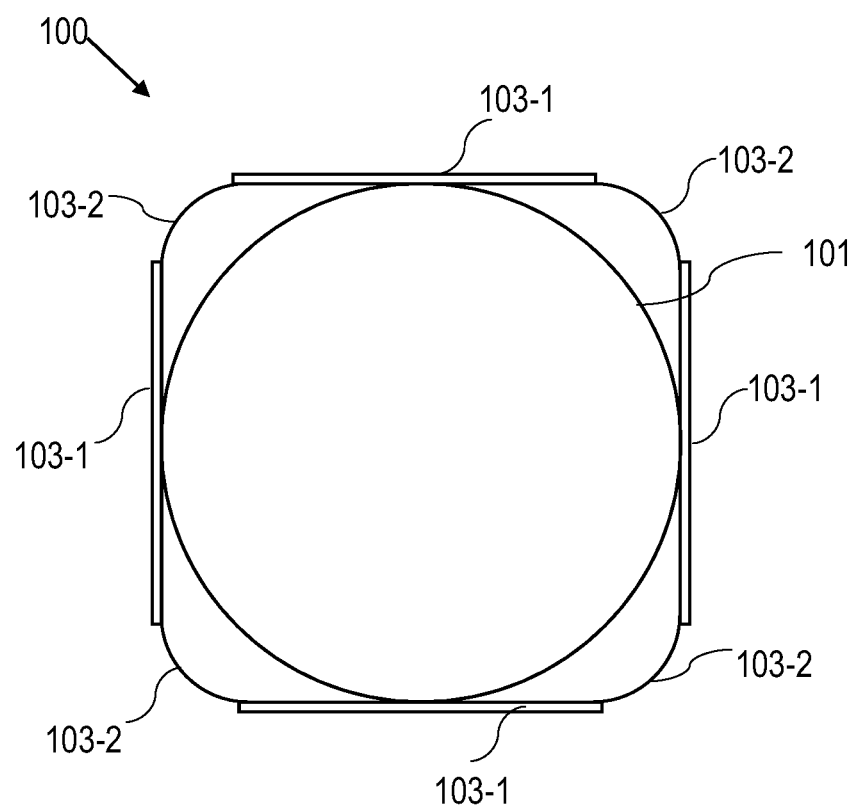
FIG. 1A shows a section view taken along a plane perpendicular to a central longitudinal axis of the power unit shown in FIG. 1.

In an embodiment, printed circuit board 103 may fully wrap around battery 101, such that battery 101 is completely disposed within printed circuit board 103 (see FIG. 1A). For example, if battery 101 is cylindrical, printed circuit board 103 may be formed into a cylinder (a similar shape) with a diameter greater than the diameter of battery 101, such that battery 101 may be completely disposed within printed circuit board 103. Printed circuit board 103 may be formed of into any shape that may fully enclose battery 101 (e.g. printed circuit 103 may be formed into a box having a height and width large enough to fully enclose battery 101). In addition to providing thermal insulation to the battery, this approach minimizes the required volume of the housing of the power unit, because the printed circuit board is formed to fit within the enclosure.

In an alternate embodiment, printed circuit board may be formed to partially cover or enclose battery 101. For example, printed circuit board 103 may be formed into a three-sided box which is disposed about battery 101, but which leaves at least a portion open on one-side. One of ordinary skill will appreciate, in a conjunction with a review of this disclosure, that printed circuit board 103 may be formed into any shape that would allow printed circuit board to at least partially cover or enclose battery 101 such that printed circuit board may contribute to insulating battery 101 during the autoclaving process.

Printed circuit board 103 may be formed from a flexible printed circuit board material, such that printed circuit board 103 may be flexibly wrapped about battery 101. In an alternate embodiment, printed circuit board 103 may be formed from a rigid circuit board material, which is either integrally formed or constructed from a plurality of panels into the desired shape. For example, printed circuit board 103 may be formed by a plurality of rectangular panels and connected together to form an enclosure with a hexagonal cross-section. In another example, printed circuit board 103 may be formed by four rectangular panels and connected into a box. In another embodiment, printed circuit board 103 may be formed from both flexible and rigid sections. For example, as shown in FIG. 1A, printed circuit board 103 may include rigid panels 103-1 that are connected by flexible portions 103-2, such that the rigid panels may be positioned and formed into the desired shape. Thus, printed circuit board 103 may provide a first layer of insulation for battery 101.

In an embodiment, insulation layer 105 may be at least partially wrapped around printed circuit board 103. In an embodiment, insulation layer 105 may be wrapped around printed circuit board 103 such that it is located between printed circuit board 103 and the inner surface of enclosure 109. In an alternate embodiment, insulation layer 105 may be inserted between printed circuit board 103 and battery 101. In yet another embodiment, power unit 100 may include two insulation layers: a first layer between the printed circuit board 103 and battery 101, and a second layer between printed circuit board 103 and enclosure 109. In any of the above embodiments, no matter where insulation layer 105 is placed, it may either fully enclose battery 101 or only partially enclose battery 101. For example, in an embodiment, insulation layer 105 is fully wrapped around printed circuit board 103. In another example, insulation layer 105 is partially wrapped around printed circuit board 103, such that insulation layer 105 does not cover a portion of battery 101.

In an embodiment, insulation layer 105 may be comprised of any thermal insulation layer suitable for insulating battery 101. For example, insulation layer 105 may be comprised of Insulfrax Thermal Insulation® available from Unifrax I LLC of Tonawanda N.Y. In an alternate embodiment, a silica aerogel insulation may be used. For example, carbon aerogel—which is a good radiative insulator because carbon absorbs the infrared radiation that transfers heat—may be used. Alternately, silica aerogel with carbon added to it—an even better insulator—may be used. Alternately, polyimide aerogel—which is an excellent insulator, is foldable in thin sheets, machineable, and is less fragile than silica aerogel—may be used. An example of such a polyimide aerogel is AeroZero® available from Blueshift 6110 Rittiman Road, San Antonio, Tex. 78218. In another embodiment, a layer of metal foil metalized mylar, or other suitable material can be used in as a reflective barrier in conjunction with another insulation layer or alone. In yet another embodiment, insulation layer 105 may be comprised of a phase change material. An example of, such a PCM insulation material, which could be molded or dispensed, is Latent Heat Storage (LHS) available from Outlast Technologies, LLC, 831 Pine Ridge Road, Golden, Colo. This type of insulation provides a low-cost, effective means for passive thermal management.

Enclosure 109 may be made any material suitable for substantially all standard autoclave cycles. Typically the enclosure 109 itself provides yet another layer of thermal isolation, although with less thermal resistance than the insulating layers within. The enclosure 109 can be made from any suitable material, such as, for example, polyether ether ketone (PEEK), polyetherimide (PEI or Ultem™) and polyphenylsulfone (PPSU or Radel®).

As described above, battery pack 100 may include connector 131, including pins 133. Connector 131 may be comprised of hermetic glass to seal pins 133, such that the battery and internal electronics of power unit 100 are not directly exposed to the extreme heat and steam environment during the autoclave process. Hermetic connector 131, with electrical pins 133, can be any hermetically sealed electric connector suitable for medical tool use. For example, hermetic glass connectors with Kovar or alloy 52 pins that have a thermal coefficient of expansion compatible with a glass header may be used. In yet another embodiment, the single cell power unit further includes a plurality of pins/sockets utilizing a type of Hyperbolic or Hyperboloid connector utilized for high vibration and high reliability applications such as available from IEH Corporation, 140 58$^{th}$ Street, Brooklyn, N.Y. It should be noted that the term pin, socket, or pin socket are used interchangeably to define one side of an electrical connection that can be separated from another side of an electrical connection. When a pin and socket are mated, an electrical connection exists between the two sides. When the pair are physically disconnected, then the electrical connection between the two sides is open. Thus, hermetic connector 131 may contain pins 133, or it may alternately contain a socket for receiving pins (e.g. from a connector associated with motorized unit 900). In an embodiment, hermetic connector 131 may have pins 133 and sockets.

In an embodiment, power unit 100 may further comprise a bulkhead 125 (shown in FIG. 9), surrounding, in a hermetically sealed relationship, hermetic connector 131. The juncture between enclosure 109 and bulkhead 125 may be hermetically sealed with an O-ring. In an embodiment, the O-ring may be a radial seal following a circular path. Furthermore, the sealing surface of the bulkhead containing the connector (i.e. the surface that abuts the enclosure) may be a radial seal O-ring following a non-circular path (i.e. stretched into a non-circular path). In an alternate embodiment, hermetic connector may extend directly from, and be hermetically sealed with, enclosure 109—without the use of bulkhead 125.

In an embodiment, the number of pins may be reduced by performing at least two independent functions with at least one of the pins. In other words, each pin—or at least one of the pins—may be configured or structured to perform multiple, unrelated functions. This may be accomplished, in an embodiment, by multiplexing different functions over the same pin.

For example, in an embodiment, two pins of pins 133 may be used together to communicate to the battery charger or factory test fixture. These pins may also be used to detect when the power unit is connected to a motorized unit, battery charger, or factory test fixture. Based on the signals that are detected on these pins the power unit may programmed to respond appropriately. In the motorized units, a resistor may be connected to these pins, whose value is measured, so the power unit can determine which motorized unit is connected and limit maximum speed or other parameters of its operation. These pins may also be used to detect when the power unit is disconnected so that the power unit can enter a sleep state to conserve battery energy when it is not needed to operate the motorized unit.

With regard to the remaining pins, in an embodiment, there may be two dedicated motor phase pins of pins 133 on the connector 131 while a third motor phase pin may act as a ground connection for the power unit when connected to a either a battery charger or factory test fixture. Another pin on the connector may be used to charge the battery under microprocessor control under normal conditions or in cases of an extremely discharged battery; it will charge the battery even when the microcontroller is not responsive. Normally the microcontroller would need to be responsive to charge the battery. This pin may also be used to reset the microcontroller in extreme circumstances. To accomplish the reset, the battery charger may apply approximately 8V to the charge pin, (or any other voltage that is higher than the normal charging voltage) for predetermined time—such as for eight seconds. If the microcontroller does not communicate with the battery charger to reduce the charging voltage within the predetermined time period, a circuit internal to the power unit may provide a hardware reset to the microcontroller. In this manner, if the microcontroller is not responsive to the external connection of the battery charger, it will be automatically reset.

Because a lower pin count may be achieved by multiplexing multiple functions over at least one pin—and thus collapsing the functionality of multiple pins into a single pin—each pin may be made larger: providing more surface area and points of contact between each pin and jack to make an electrical connection, and improving reliability. The larger pins can also accommodate more mechanical tolerance between the pins and jacks. The larger pins may also heat less at a given motor current than smaller pins, further improving reliability. Furthermore, the minimized pin count may reduce the heat transfer from the autoclave into the enclosure because of the smaller overall diameter of the connector and less cross sectional area from the pins—keeping the battery and electronics at a lower peak temperature during the autoclave cycle and improving reliability. Reducing the number of pins in the connector may also improve the reliability of the electrical connection between the power unit 100 and the motorized unit 900. Finally, because each pin in the connector has a potential of an electrical open or failure, reducing the number of pins reduces the probability of a contact failure.

Power unit 100 may comprise a one-way pressure check-valve 141 so that the vacuum may be created within enclosure 109. One way check-valve 141 may be in communication with the interior of enclosure 109 and an exterior of enclosure 109, such that check valve 141 may refresh the vacuum within power unit 100 each time the power unit 100 is run through an autoclave cycle with vacuum pumping as part of the autoclave sterilization process. The vacuum may provide yet another aspect of thermal isolation between the outside surface of the power unit casing and the single high temperature battery cell disposed within the power unit by limiting both thermal conduction and thermal convection between the single battery cell and the outside surface of the power unit housing. For example, a U shaped check-valve such as 626-115 available from Precision Associates, Inc. of Minneapolis, Minn., may be used.

One of ordinary skill should appreciate, in conjunction with a review of this disclosure, that the U-shaped check-valve 141 shown in FIG. 1 is only one embodiment of a low pressure one way check-valve that can be used to pull a vacuum within the otherwise hermetically sealed power unit enclosure 109. Other examples of check valves that may be used include ball check valves, umbrella check valves and duckbill check valves.

Battery 101, in an embodiment, may be a single-cell battery, allowing power unit 100 to remain relatively light and compact. Furthermore, in an embodiment, battery 101 may be a high-temperature battery (such as capable of withstanding over 100° C.) able to withstand the temperatures of the autoclaving process without overheating. For example, battery 101 may be a lithium ion ceramic cell, such as those developed for Formula 1 racecars. Such single cells batteries are relatively high power-density and are capable of withstanding high temperatures. Multiple smaller high power density, high temperature tolerant batteries are also contemplated herein. Indeed, one of ordinary skill will appreciate that multiple, smaller batteries (or even multiple similarly sized batteries, or large batteries, although this will result in a heavier and harder to maneuver device) may be used in place of a single-cell battery, as long as the batteries may be used in handheld, medical, powered devices.

The high temperature batteries (e.g. Lithium ion ceramic cells) as described above, have a relatively high temperature tolerance, for example, to survive without damage, high charge and discharge currents associated with kinetic energy recovery systems (KERS), as used in cars. Yet, if mounted alone in standard medical grade battery housings, these cells still could not survive most standard autoclave cycles without further protective means. In an embodiment, the high temperature battery may have a low internal impedance, such that it is capable of producing 22 A at 2.5 V while nearly discharged. One of ordinary skill will appreciate, in conjunction with a review of this disclosure, that any suitable high energy density single cell can be used, such as, for example a single Lithium ion cell including a high temperature chemistry such as LIPON (lithium iron phosphorus oxyntride), and solid electrolyte from solid electrolyte types, such as LSPS (lithium tin phosphorus sulfide). Furthermore, one of ordinary skill will appreciate that the temperatures that battery 101 can withstand is dependent, in part, on the insulation provided by power unit 100. In other words, battery 101 need only withstand temperatures permitted by the insulation structure described in this disclosure (or other insulation structure not described herein).

However, most single-cell batteries are only capable of producing voltages within the 3.3-3.6 V, which is insufficient for most standard portable medical tool motors. Accordingly, in an embodiment, a boost converter may be added to increase the voltage provided to motorized unit 900. Such a boost convert topology is known in the art and may be optimized for the small size, weight, and power efficiency of power unit 100. In an embodiment, the converter may raise the voltage to 10 V or higher. In an embodiment, the boost convert, together with a single-cell battery with a low internal impedance—such as a Lithium-ion ceramic battery—may produce 50 W of power to drive motorized unit 900. In an embodiment, the combination may provide approximately 5 A of current.

Figure 15:
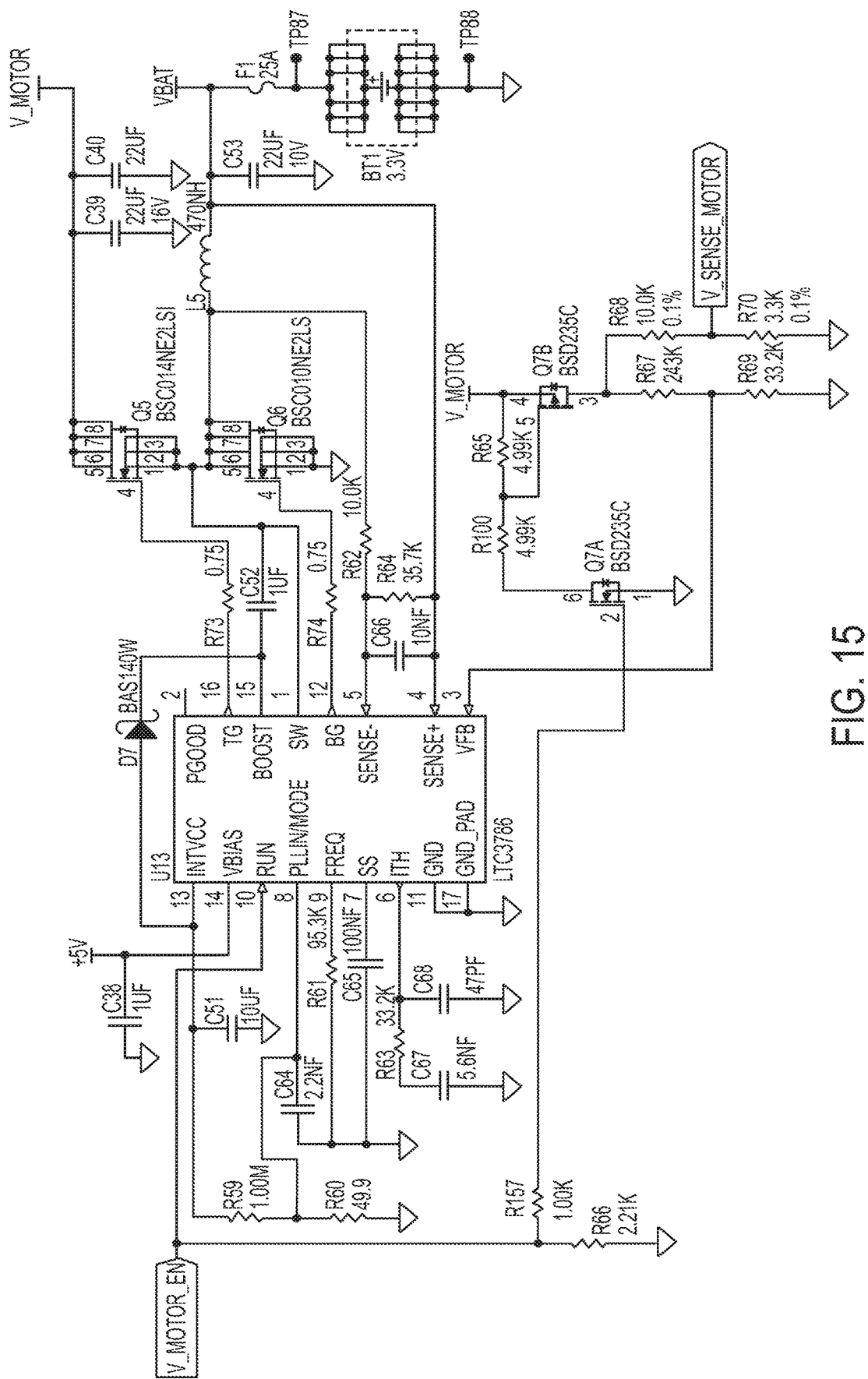
FIG. 15 a circuit schematic of boost converter, according to an embodiment.

FIG. 15 shows an example of such a converter. As shown in FIG. 15, the high side commutation transistor Q5 integrates a Schottky diode (or a diode that performs similar to a Schottky diode) to minimize voltage drop while the controller U13 has this transistor turned off to improve efficiency. The efficiency allows longer run time and reduces heat generated within the power unit to improve reliability. The bottom transistor Q6 does not include this Schottky-like diode to reduce battery quiescent current while the converter is turned off. The feedback resistor divider R67 and R69 is also disconnected by Q7B while the converter is turned off to minimize battery quiescent current. Reducing battery quiescent current allows longer time between battery recharges while unused.

In an embodiment, battery 101 may be directly attached to printed circuit board 103. In an embodiment only the positive terminal is directly attached to printed circuit board 103. In an alternate embodiment, both the positive and negative terminal is directly attached to printed circuit board 103. In an embodiment, battery 101 may be attached by tabs welded, soldered, or otherwise connected (i.e. to allow the flow of current), to its ends and which are directly soldered to the PCB—the tabs being sized and dimensioned to mitigate a ripple in the voltage supplied by battery 101. In an embodiment, the area between the tabs contains the boost circuit and 3-phase motor inverter (driver) to best utilize space between the tabs and reduce the need for capacitance on the input side of the boost converter. If battery 101 is separated from printed circuit board—and is attached, for example, by wires—ripples may form in the voltage provided by battery 101. Such ripples may be mitigated with, for example, a large capacitor (i.e. a filter). However, directly attaching battery 101 reduces the need for such a large capacitor. Furthermore, directly connecting battery 101 to the printed circuit board efficiently uses the space within enclosure 109 and avoids the use of extra components and wires.

As an example, power unit 100 as described above may be made as follows. Single cell Li ion battery 101 may reside within and at about the center of the power unit enclosure 109. Any suitable high energy density single cell can be used, such as, for example a single Li ion cell including an internal ceramic structure for relatively high charge and discharge currents. In some prototype implementations, the AHR18700m1Ultra battery available from A123 Systems of Watertown, Mass. has been used. Surrounding the battery may be a rigid/flex flexible PCB 103 which includes control electronics described in more detail herein. Surrounding flexible PCB 103, there may be one or more layers of any suitable insulation 105 disposed between the flexible PCB 103 and the inner surfaces of the power unit enclosure 109. In some prototype implementations, the insulation used was ⅛" Insulfrax paper, available from Unifrax I LLC of Tonawanda, N.Y. The power unit enclosure 109 can be made from any material suitable to withstand standard autoclave temperature and pressure cycles. In some prototype implementations, the power unit enclosure 109 was made from Ultem™ 1000 available from Sabic (Saudi Basic Industries Corporation) of Pittsfield, Mass.

Figure 9:
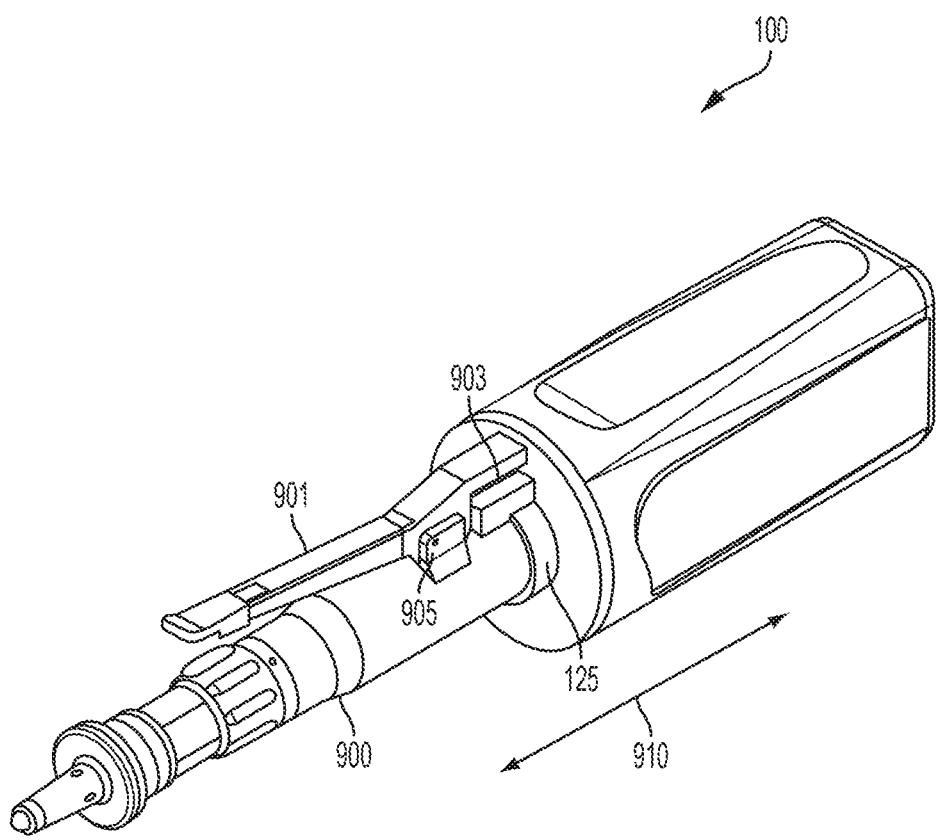
FIG. 9 shows an isometric drawing of one exemplary embodiment of a surgical handpiece tool having a power unit and a motorized unit, according to an embodiment.
Figure 10:
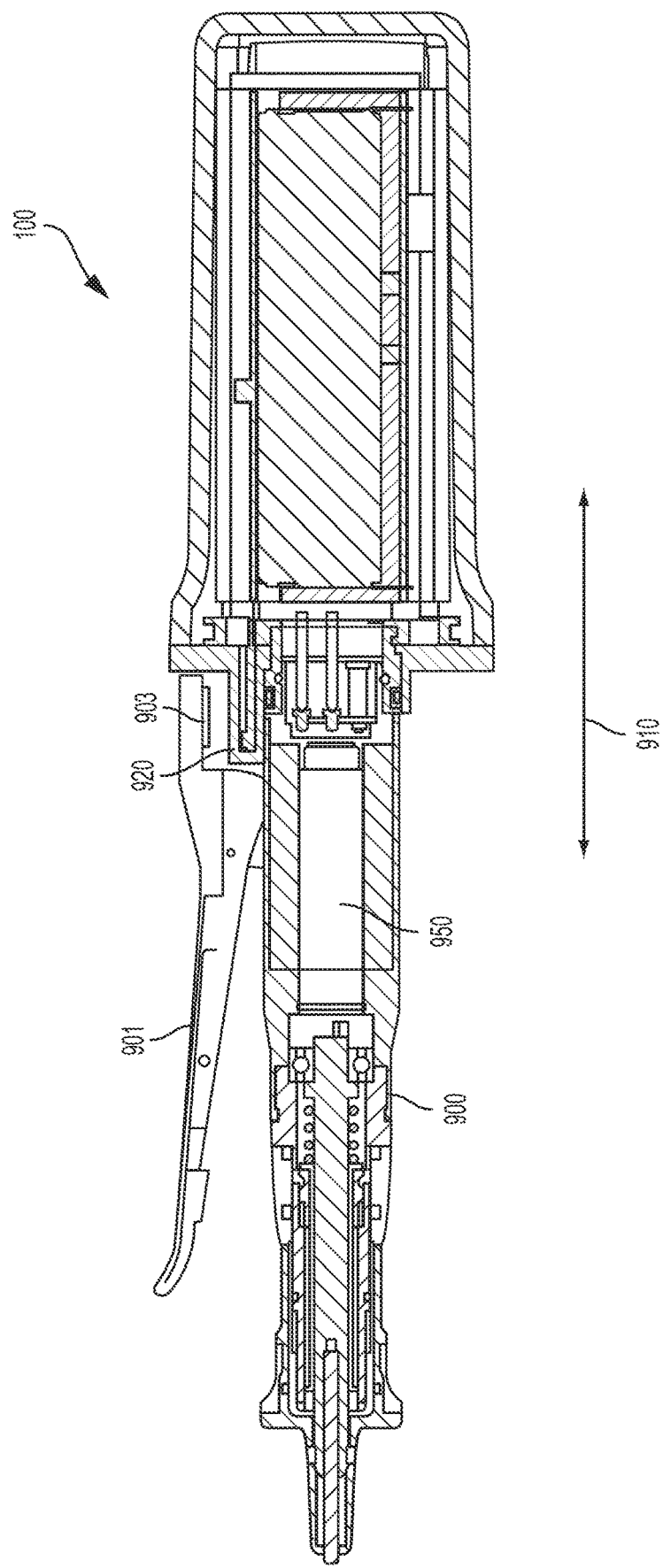
FIG. 10 shows a section view of surgical handpiece tool having a power unit and a motorized unit of FIG. 9, according to an embodiment.

As shown in FIG. 9, according to an embodiment, power unit 100 may be configured to mate with and operatively connect to a motorized unit 900. Motorized unit 900 may include a motor 950 (shown in FIG. 10) for powering a surgical implement. In an embodiment, motor 950 may receive power from, and be operated according to signals received from pins 133. One of ordinary skill will appreciate that power unit 100 can couple to any number of motorized units—including other DC powered medical devices—and motorized unit 900 is only an embodiment of one such possible attachment. Other attachments may include, but are not limited to, medium and high speed drills, as well as sagittal, oscillating, and reciprocal saws.

As per arrowed line 910, power unit 100 may be detached from motorized unit 900 for any reason, such as replacing power unit 100, replacing battery 101, sterilizing each part, etc. Any suitable structure known in the art can be used to removably attach power unit 100 to motorized unit 900. For example, a frictional type "click" latching mechanism can be based on a canted spring latch. An example of such canted springs—which may be disposed, for example, in a groove in the shell of the power unit—are available from the Bal Seal Engineering, Inc. of Foothill Ranch, Calif.

According to an embodiment, the motor speed may be controlled based on the position of lever 901 about pivot point 905. More particularly, the proximity of magnet 903 to sensor 920 may dictate the speed of motor 950. According to an embodiment, as lever 901—which may be spring biased to an open position where lever 901 is farthest from the motorized unit 900—is pressed towards the motorized unit 900, magnet 903 moves away from magnet sensor 920 (e.g. a Hall sensor) disposed in the shell of the power unit 100. As the distance of magnet 903 from sensor 920 increases, the motor controller may cause the motor speed of motorized unit 900 to decrease (or, in an alternate embodiment, to increase). More particularly, as the strength of the magnetic field produced by magnet 903 and sensed by magnet sensor 901 increases, or decreases, the speed of the motor may vary. For example, as the strength of the magnetic field sensed by sensor 920 increases, the speed of the motor may decrease.

One of ordinary skill will appreciate that the configuration and position of lever 901 may be altered. For example, in an alternate embodiment, sensor 920 may be disposed in power unit 100 and magnet 903 may be disposed on lever 901. Further, in an alternate embodiment, lever 901 may be mounted on power unit 100. In yet another embodiment, lever 901, magnet 903, and sensor 920 may be each be disposed on power unit 100.

To avoid unintentionally engaging motor 950 while power unit 100 is separated from motorized unit 900, magnet 930 may be sized, dimensioned, and positioned such that sensor 920 can remain substantially close to magnet 903 while the two units are pulled apart in an axial direction (along arrowed line 910). In an embodiment, magnet 903 may be long enough that—while power unit 100 is being disengaged from motorized unit 900—sensor may continue to sense the magnetic field of magnet 930 until motorized unit 900 is completely detached from power unit 100. Thus, motor 950 is configured to not begin to rotate as the motorized unit is pulled from power unit along arrowed line 910.

In an alternate embodiment, as shown in FIG. 2, power unit 100 may include a wireless transceiver—in communication and controlled by printed circuit board 103 or a separate controller—capable of communicating with a control device outside of the power unit. Wireless transceiver 121, and the associated control circuit, may communicate with the exterior control device via any communications protocol known in the art. Using the wireless transceiver, control device may control the speed of the motor attached to power unit through, for example, a foot pedal pressed by a user. Alternately, the transceiver may be used to connect to a computing device, such as a smart phone or tablet, laptop, desktop computer, or server. The connected mobile phone or computing may be used to set any of a number of possible settings (e.g., maximum or minimum speed of the motor), to view measured metrics (e.g., battery levels) or to control the device (e.g., controlling the speed of the motor with a mobile device).

The wireless communication/transmission can be over a network, which can be any suitable wired or wireless network capable of transmitting communication, including but not limited to a telephone network, Internet, Intranet, local area network, Ethernet, online communication, offline communications, wireless communications and/or similar communications means. The wireless transmission can be accomplished through any wireless protocol/technology, including, but not limited to, ZigBee standards-based protocol, Bluetooth technology, and/or Wi-Fi technology. The devices can be located in the same room, in a different room in the same building, and/or in a completely different building and location from each other. A user using a host computer (or a different computer) can send data transmission, control or communication signals to the power unit 100 to initiate or perform any of the functions described herein.

Figure 11:
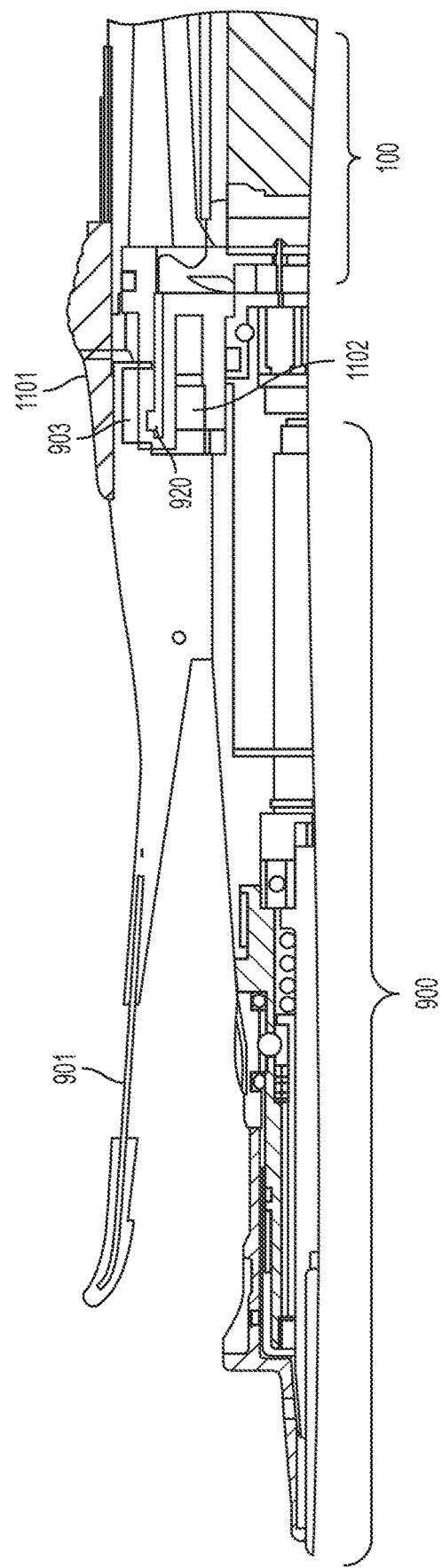
FIG. 11 shows a partial section view of an exemplary embodiment of a motorized surgical tool with a safety switch, according to an embodiment.

FIG. 11 shows a partial section view of an embodiment of a motorized unit 900. As shown, motorized unit 900 may comprise a safety switch 1101, configured to override the motor speed control function of lever 901. In an embodiment, safety switch 1101 includes a magnet 1102 which interacts with the magnetic field sensor on the power unit. When the safety switch 1101 magnet 1102 is moved axially (e.g. by sliding) so that magnet 1102 is adjacent to sensor 920, safety switch 1101 magnet 1102 saturates sensor 920 rendering sensor 920 incapable of detecting any change in the magnetic field of the lever 901 magnet 903, such that motor 950 will remain off regardless of the position of lever 901. Furthermore, in an embodiment, safety switch 1101 may mechanically interfere with lever 901—when engaged in the safe position—obstructing the movement of lever 901 in order to provide further feedback to the user that the device is in an inoperative state.

Figure 12:
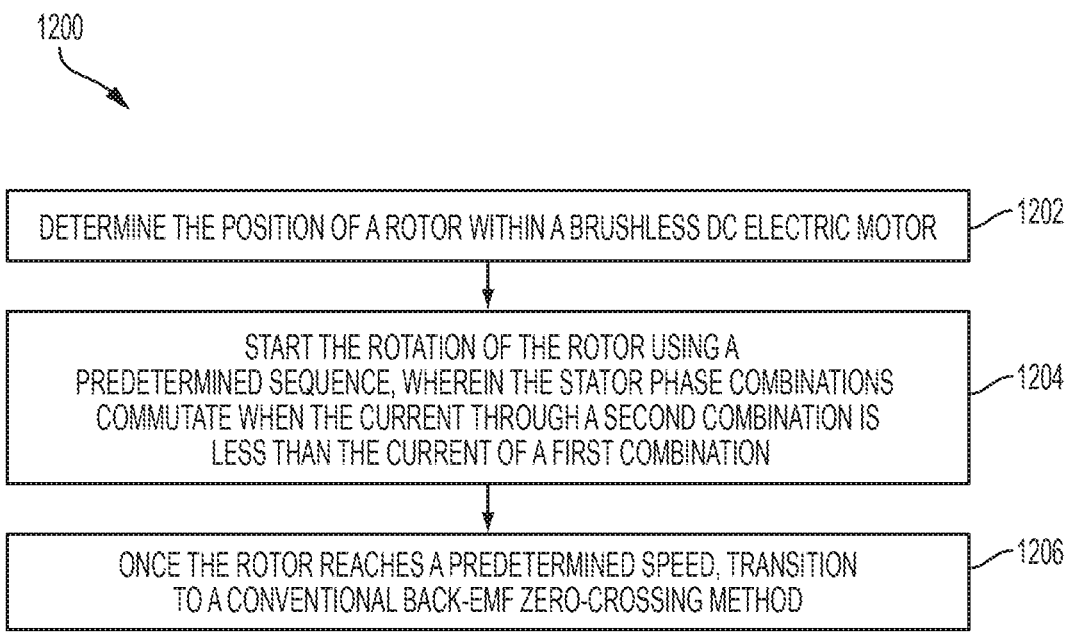
FIG. 12 shows a flow chart of a startup method for an electric motor, according to an embodiment.

Referring now to FIG. 12, there is shown an embodiment of a method 1200 (or algorithm) for smoothly starting—i.e., without an accompanying jerk—a brushless DC (BLDC) motor. In an embodiment, method 1200 may be implemented by a BLDC motor, such as motor 950 as described in this disclosure, in conjunction with a processing unit programmed to execute the steps of method 1200, such as the processor described in conjunction with power unit 100. While method 1200 is described in connection with power unit 100 and motorized unit 900, one of ordinary skill will appreciate, in conjunction with a review of this disclosure, that this method may be implemented with any BLDC motor in any context where a smooth startup is required or otherwise desirable.

At step 1202, in an embodiment, the static rotor position of a BLDC motor may be determined. In one embodiment, this may be accomplished by turning the rotor electrically from its initial, unknown position to a second, known, static position. However, moving the rotor to the known position may itself cause an undesirable jerking of the handle since it requires the rotor to first rotate from an unknown position. In another embodiment, the static position of a rotor may be determined, by sensing, such as with a Hall Effect sensor, the rotor's position according to methods known in the art. In yet another embodiment, the rotor's position may be determined by comparing the relative current drawn through different phase combinations. Such a method has been described in "Start-up Control Algorithm for Sensorless and Variable Load BLDC Control Using Variable Inductance Sensing Method," (AP08018), by Infineon Technologies AG of Munchen, Germany, the entire disclosure of which is herein incorporated by reference and briefly described below.

According to this embodiment, the static rotor position may be determined by measuring the current drawn by each phase-combination in response to a test voltage. Because the permanent magnets of the rotor will affect the inductance of each phase, each phase-combination will draw a different current in response to the test voltage. (Further, because the pulses applied to the coil are of a very short duration, the motor rotor does not move any significant amount and therefore the surgeon holding the tool does not feel any jerking during this static position sensing step.) Thus, for example, in a three phase BLDC motor, a test voltage may be applied to phase A, while phases B and C are grounded and the resulting current measured. Next, the process is reversed such that A may be grounded while a test voltage is applied to B and C and the resulting current again measured. The process may be started again with phase C: a test voltage may be applied to C while A and B are grounded, etc. This may be repeated until the current drawn by all phase combinations (6 total for three-phase BLDC motor) has been measured.

One of ordinary skill will appreciate, in conjunction with a review of this disclosure, that other BLDC motors may have more, or fewer, phases, and each phase may be tested. Accordingly, a BLDC motor with six phases may have twelve testable combinations. One of ordinary skill will also appreciate that it is not necessary to test each testable combination; although, testing fewer combinations will result in a courser measurement of the rotor's position, and it is thus advantageous to test the maximum possible combinations.

When comparing the resulting currents, each phase combination may be compared to its reverse: thus, the current associated with phase A high and B and C low may be compared to the current associated with phases B and C high and A low. The larger current may be assumed to be traveling in the direction of the magnetic field. Thus, if the current associated with A high and B and C low is higher than the current associated with B and C high and A low, the magnetic field is in the direction of the current traveling from phase A to B and C, and it may be assumed that the north pole of the rotor is nearer to phase A than to phases B and C. Therefore, the position of the rotor may be narrowed by approximately 180°. Performing a similar comparison with each other phase combination will narrow the location of rotor to within 60°. BLDC motor combinations with more phases, and thus more phase combinations, may narrow the location of the rotor to within 30° or even smaller ranges.

Figure 3:
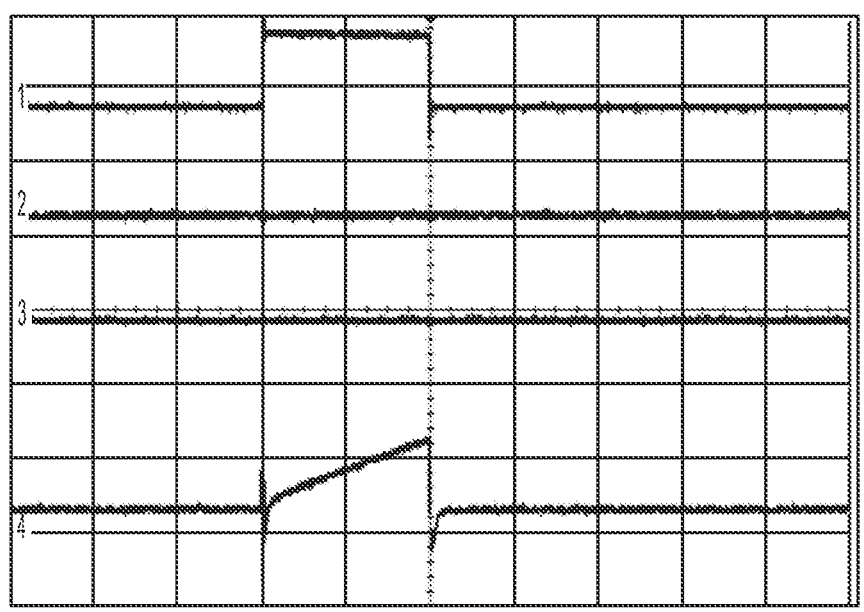
FIG. 3 shows a voltage pulse and current measured for determining motor static rotor position, according to an embodiment.

FIG. 3 shows an example voltage pulse on Phase A (trace 301) while Phase B (trace 303) and C (trace 305) are held low. For step 1202, the current is the triangular waveform (trace 307). The horizontal time scale is 5 μs/div. The current may be measured by the use of a high-speed amplifier placed across a low-value shunt resistor. The polarity of the phases may then be reversed for an equal and opposite pulse to avoid magnetization of the stator core. Then the same procedure is done for Phase B and then C for a total of six pulses. Depending on the relative magnitude of the pulses, a lookup table may tell in which of the six possible commutation combinations, or sectors, the rotor lies. Each combination is repeated twice during a mechanical rotation of the rotor, so there are 12 sectors, and therefore 12 commutations, per full revolution.

At step 1204, once the rotor position is known, a predetermined power sequence can begin to drive rotor in a desired direction. In an embodiment, at least one phase (i.e. the phase that correlates with the current location of the rotor) may be powered. In an embodiment, the phase may be powered by a pulse-width modulated voltage (e.g. a square wave). In an embodiment, more than one phase may be driven at a time.

Figure 4:
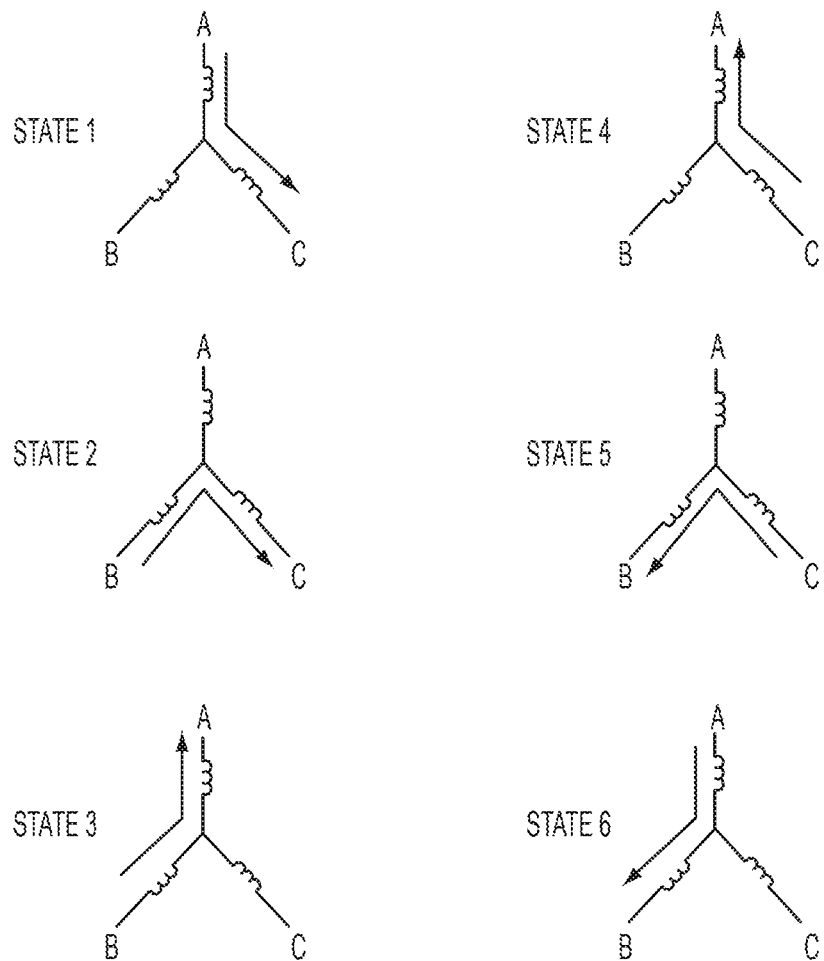
FIG. 4 shows a commutation pattern, according to an embodiment.

For this discussion, it is useful to first describe a typical commutation pattern of a three phase BLDC motor. One of ordinary skill will appreciate that the commutation pattern described herein is just one of many possible patterns. For a three phase electric motor, during one full rotation of the rotor, the motor may commutate between six different phase combinations. For the purpose of this disclosure only, the combination A-B shall be understood to mean that phase A is coupled to the voltage source while B is coupled to ground. Conversely, B-A shall be understood to mean that phase B is coupled to the voltage source while A is coupled to ground, and so forth. The active phase combinations during any given period of time may be referred to as a "state." Thus, as shown in FIG. 4, during the full rotation of the rotor, the motor may commutate from phase to phase in the following order:

TABLE 1

Single Phase Combination Commutation Pattern

| State | Phase Combination |
|---|---|
| State 1 | A-C |
| State 2 | B-C |
| State 3 | B-A |
| State 4 | C-A |
| State 5 | C-B |
| State 6 | A-B |

Figure 5:
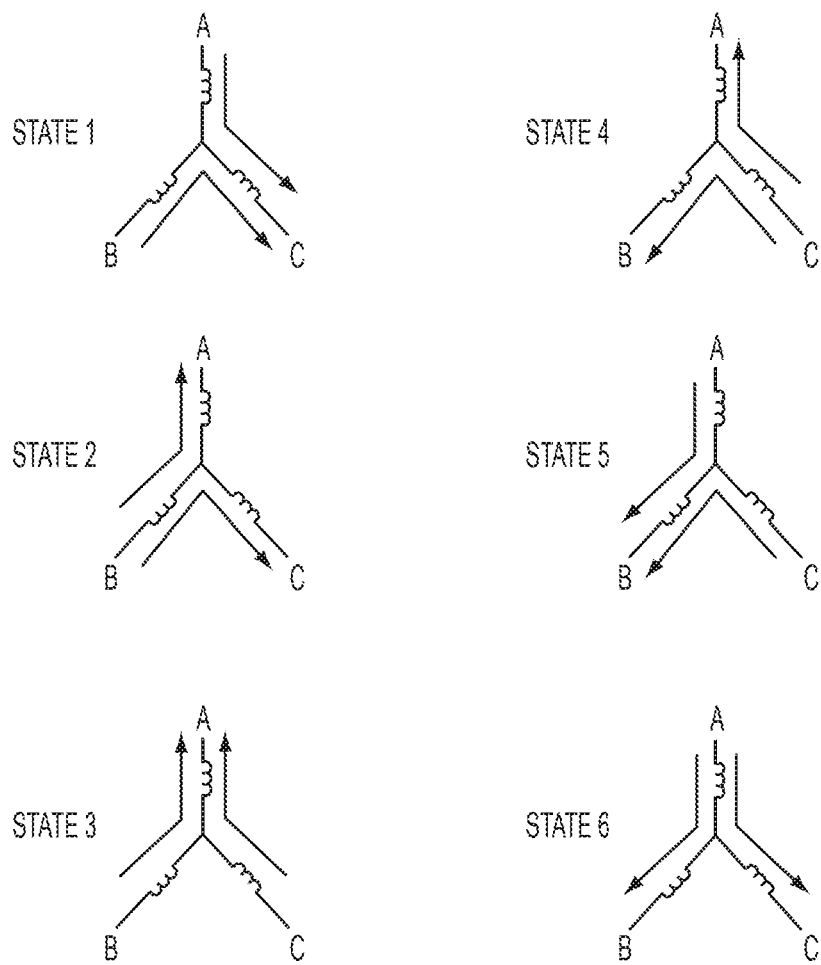
FIG. 5 shows a commutation pattern, according to an embodiment.

However, at any given point during the rotation, at least two phase combinations may add positive torque to the rotor. For example, when a rotor approaches a certain point in its path, both the "present" phase combination (i.e. the phase combination that adds the greatest torque to rotor) and the "next" phase combination (i.e. the phase combination that is scheduled to begin next) will add positive torque to the rotor. (This explanation assumes that the necessary current directions and phase combinations have been preselected into an advantageous commutation pattern that initiates a "present" phase combination and schedules a "next" phase combination, an example of such a commutation pattern may be seen in TABLE 1 above.) For example, if motor 950 is in state 1, and rotor is being driven by phase combination A-C, at some point during the rotor's rotation, both A-C and B-C (i.e. both the present phase combination and the next scheduled phase combination) will add positive torque the rotor. Furthermore, once, the rotor moves into state 2, at some point during the rotor's rotation, A-C will cease adding positive torque to the rotor and, instead, B-A (of state 3) will begin to add positive torque. According to an embodiment, the phase combinations may be thus powered as shown in FIG. 5, and according to the following table:

TABLE 2

Dual Phase Combination Commutation Pattern

| State | Phase Combination 1 | Phase Combination 2 |
| --- | --- | --- |
| State 1 | A-C | B-C |
| State 2 | B-C | B-A |
| State 3 | B-A | C-A |
| State 4 | C-A | C-B |
| State 5 | C-B | A-B |
| State 6 | A-B | A-C |

Thus, for a given state, both the "present" and the "next" phase combinations may be powered. Of course, for motors having more than three phases, any number of phase combinations that add positive torque to the rotor may be powered at any given point in time.

According to one embodiment, both phase combinations may be powered with a substantially constant voltage. In another embodiment, both phase combinations may be powered with an alternated pulse-width modulated signal. In other words, the pulses of the pulse-width modulated signal may be alternated between each phase combination. For example, if, for a given rotor position, the two powered phase combinations are A-C and B-C, the first pulse of the pulse-width modulated signal may be delivered to A-C, the second pulse to B-C, the third pulse to A-C, etc. Furthermore, the pulses need not be directly alternated between each phase-combination, but rather may be divided in any proportion between the phase-combinations. For example, for every four pulses delivered to one of the phases, only one may be delivered to the other. The proportion and order of the phase pulses may also be varied over time or as the rotor progresses from one phase and toward another. One of ordinary skill will appreciate, in conjunction with a review of this disclosure, that power may be delivered to according to other modulation schemes, and any such suitable scheme may be used to divide power between the pairs of phase combinations.

As the rotor progresses around its path, and moves toward and then away from each phase, it is of course necessary to commutate between different phase combinations pairs. For example, as shown in Table 2 above, and in FIG. 5, at some point, motor 950 will commutate from State 1, where A-C and B-C are receiving power, to State 2, where B-C and B-A receive power.

Figure 14:
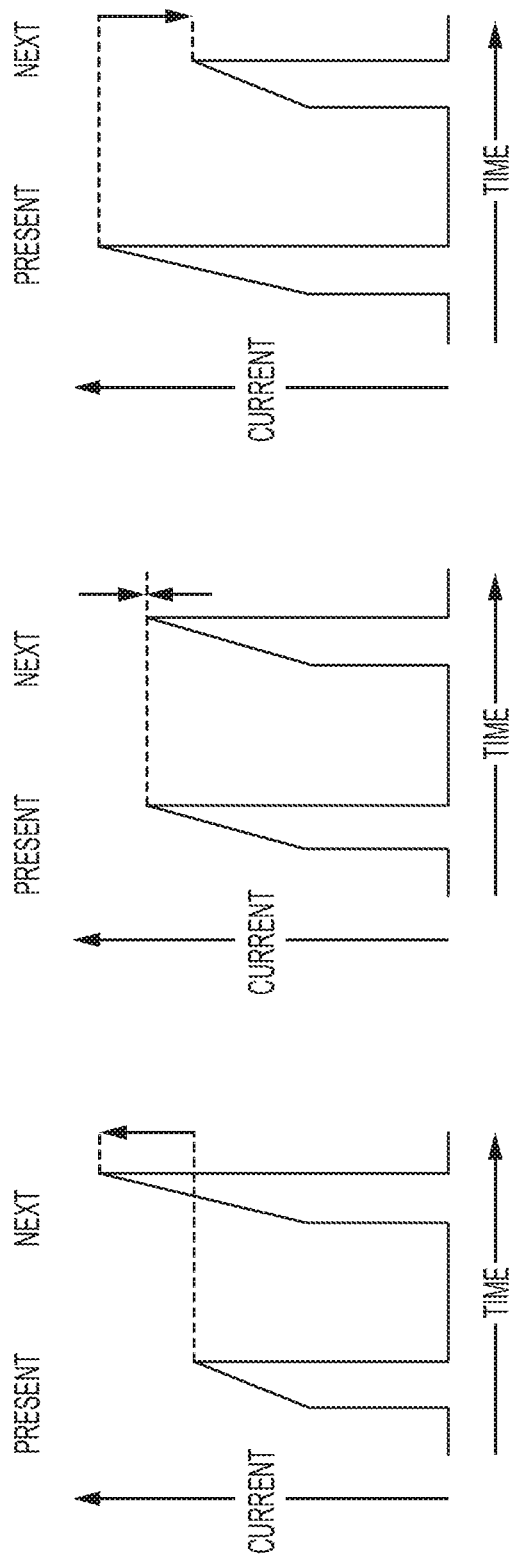
FIG. 14a is a graphical illustration showing current of a certain phase according to an embodiment.
FIG. 14b is a graphical illustration showing current of a certain phase according to an embodiment, and FIG. 14c graphical illustration showing current of a certain phase according to an embodiment.

Thus, motor 950 commutates from a first phase combination pair to a second phase combination pair. In an embodiment, the commutation may occur when the current drawn by the "next" phase combination falls below the current drawn by the "present" phase combination. One of ordinary skill will appreciate that for most BLDC motors, the inductance of a given phase combination increases as the rotor magnet approaches it, and the rate of change of current therefore decreases. The opposite occurs as the rotor passes the phase combination and the distance increases. As the inductance of the "present" phase combination falls, the inductance of the "next" phase combination rises. The effect on phase current during this rotation is illustrated in FIG. 14 *a, b* and *c*. In FIG. 14*a*, the rotor magnet is closer to the "present" phase combination than the "next" phase combination. In FIG. 14*b*, the rotor is equidistant between the two phase combinations. In FIG. 14*c*, the rotor is now closer to the "next" phase combination. Accordingly, motor 950 may commutate from a first pair of phase combinations to the next pair of phase combinations when the current of one of the phase combinations drops below the current of the other.

Stated differently, in a three-phase BLDC motor and as described above, a given pair of phase combinations may be conceived of as having a "present" phase combination and a "next" phase combination. In an embodiment, the commutation may occur when current of the "next" phase combination drops below the current of the "present" phase combination. At this point, the "next" phase combinations becomes the "present" phase combination, while the upcoming scheduled phase combination becomes the "next" phase combination, and the original "present" phase combination is no longer powered. For example, if during a given state, the phase combinations A-C and B-C are powered, the current drawn by each may be monitored. When the current drawn by B-C falls below the current drawn by A-C, the motor may commutate to the next state: ceasing to power A-C, and instead beginning to power B-A in addition to B-C. Thus, in an embodiment, both pairs of phase combinations (i.e. each consecutive state) share at least one pair of phase combinations. In the first state of any commutation, the common combination is the "next" phase combination, and in the second state, the common combination is the "present" phase combination. This method of commutating will result in a smooth transition between states, which is particularly beneficial at low speeds.

One of ordinary skill in the art will appreciate that the commutation does not need to occur at the precise moment that the current in the "next" phase combination falls below the current of the "present" phase combination. Instead, the commutation may occur if the "next" current is substantially equal to, or within a defined percentage of the "present" current. For example, if the current of the "next" phase combination is within 10% of the "present" phase combination, the motor may commutate to the state. In an alternate embodiment, the commutation may occur within predetermined time period after the current of the "next" phase falls below (or is substantially equal to, or within a defined percentage of) the current of the "present" phase combination. In an alternate embodiment, the commutation may occur after the "next" current has fallen below the "present" current for a given number of pulse pairs.

Figure 6:
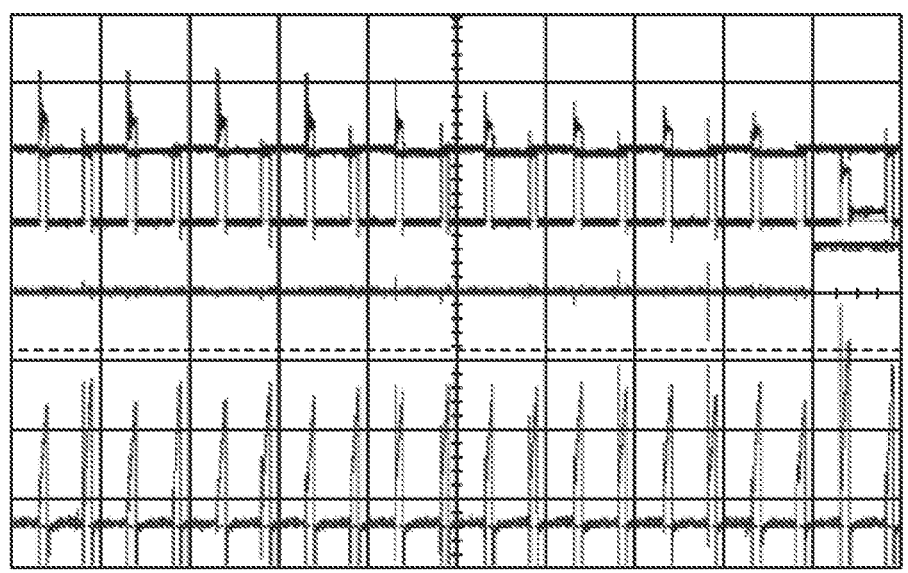
FIG. 6 shows present and next phase voltages, according to an embodiment.

FIG. 6 shows an example "present" phase combination B-C, while the "next" phase combination is B-A. For clarity, Phase C has been substituted for a signal indicating when the software has decided to commutate. Starting at the left, it can be seen that the odd sequence numbers ('present') are at first smaller than the even ones ('next'), then the same, and then finally greater. When the 'next' has been less than 'present' for a number of pulse pairs for confirmation, commutation occurs.

The described method is less than optimal in efficiency, which is obtained when the motor is powered by the "present" phase combination. Above a certain speed, which varies for a given motor, another method called Back-EMF zero-crossing detection may be employed. As a motor turns, the rotation of the rotor magnets interacts with the coils of the stator to form a generator.

Figure 7:
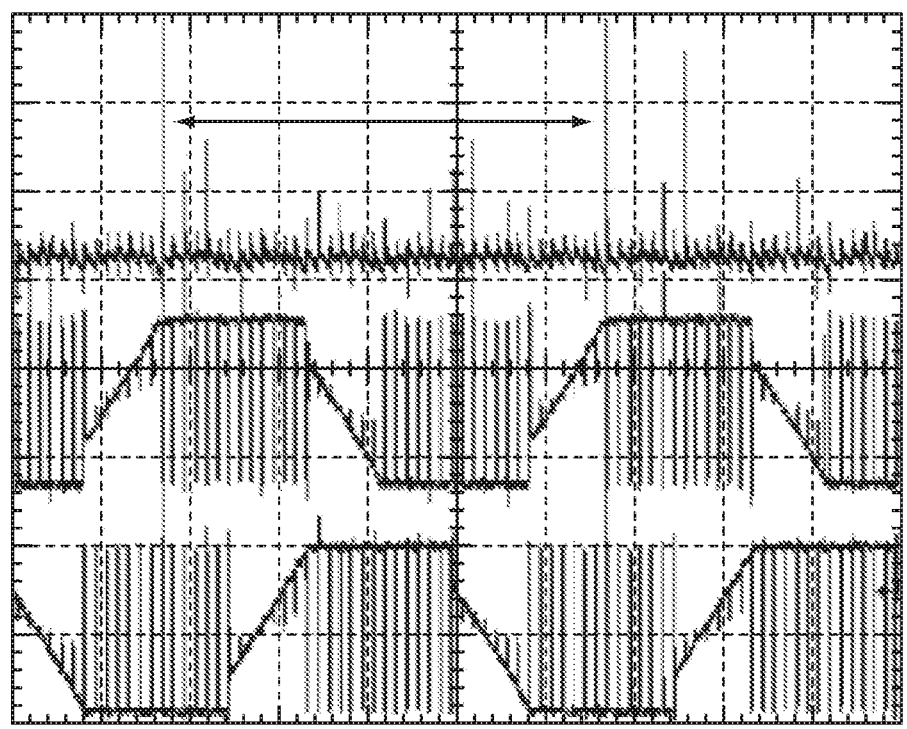
FIG. 7 shows rising and falling waveforms, according to an embodiment.

FIG. 7 shows exemplary rising and falling waveforms (about 1 ms between the two vertical time cursors). (Note that this figure shows a slightly different modulation scheme from the others—bipolar as opposed to unipolar—for clarity.) The generated voltage rises with increased speed, such that the maximum motor speed, 30,000 RPM at 10V in this case, is obtained when the generated voltage is equal and opposite to the applied voltage i.e. it is a back voltage as it opposes rotation. In normal motor operation only two of the three phases are energized at a time, and this back-EMF can be observed on the third phase. When the rising or falling waveform crosses the midpoint of the supply voltage, the rotor is halfway between the last commutation point and the next, and it is straightforward to use a timer to determine exactly when the commutation should occur.

In an embodiment, the upcoming scheduled phase combinations may be retrieved from memory where they are stored in a look-up table or some other advantageous storing scheme.

Furthermore, one of ordinary skill in the art will appreciate, in conjunction with a review of this disclosure, that this method may be expanded out for any number of phases and phase combination.

In step 1206, once the motor 950 rotor speed passes a predetermined angular speed, the operation of the motor, in an embodiment, may transition to a more conventional voltage commutation method. The angular velocity of the rotor may be determined by measuring the time between each commutation, and thus measuring the speed at which the rotor passes through each sector. Once there is sufficient voltage generated by the permanent magnet of the rotor passing the windings of the motor stator, so that a voltage of a phase of the three phases not being powered during any given period between commutations can be used as a feedback signal to control motor speed. In an alternate embodiment, the commutations may continue to occur substantially at the time the "next" phase current drops below the "present" phase combination current, regardless of the angular velocity of the rotor.

Figure 8:
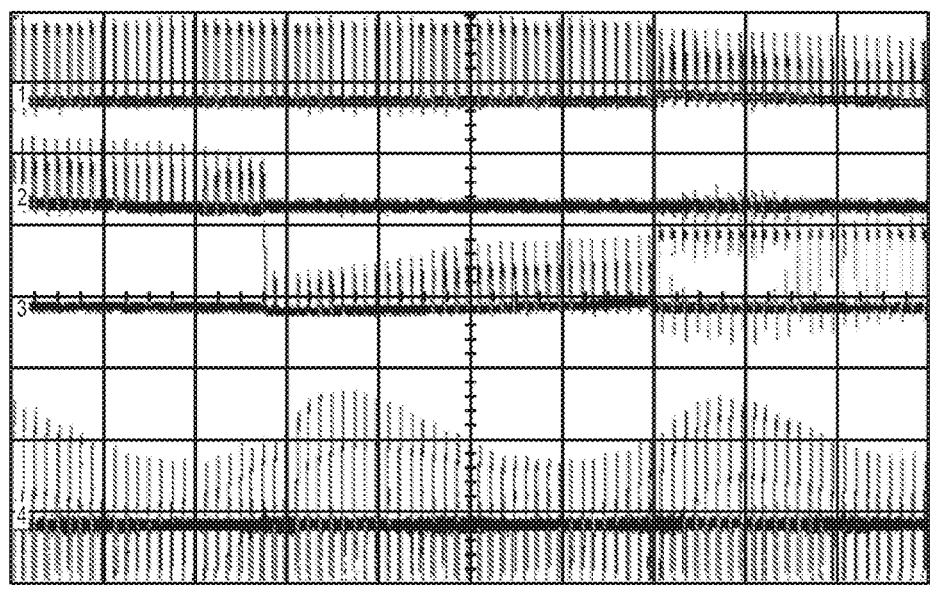
FIG. 8 shows a number of commutations using a more conventional switching scheme, according to an embodiment.

FIG. 8 shows a number of commutations in more detail (200 μs/div) using a more conventional switching scheme. All the waveforms are chopped due to the PWM. In the center, the rising waveform can be seen on the open Phase C, while Phase A is energized, and Phase B is grounded. Also, the variation of current within a sector can be seen, as well as the pronounced phase shift of the peaks with respect to the commutation point.

Figure 13:
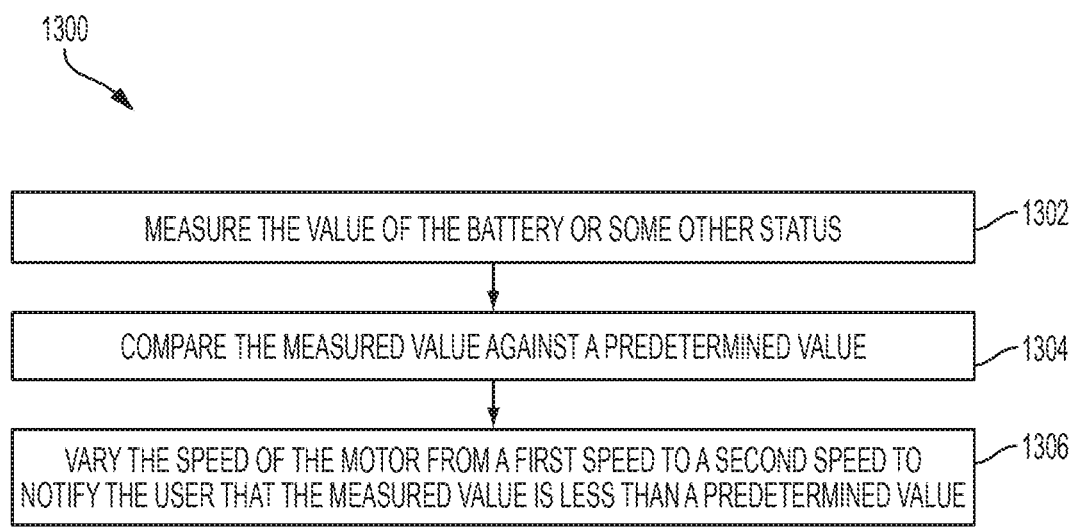
FIG. 13 shows a flow chart for communicating, with the motor, a status or other message, according to an embodiment.

FIG. 13 shows an embodiment of a method 1300, or algorithm, for notifying a user of a low battery (or other message, in alternate embodiments). In step 1302, the status of battery 101 or another status is measured. For example, the current voltage produced by battery 101 may be measured. In an alternate embodiment, a metric indicating the proper functioning of motor 950 may be measured.

In step 1304, the measured value may be compared against a predetermined value. For example, if the voltage produced by battery 101 is measured in step 1302, it may then be compared against a predetermined voltage value to determine if the battery is low. Alternately, the current may be integrated over time and measured against a predetermined value to monitor the charge of the battery.

If the battery is low (or the other measured status requires the notification of the user), in step 1306, the speed of the motor may be changed according to a noticeable pattern, to inform the user of the low battery. For example, motor 950 may begin at a first velocity and after a predetermined period of time, change to a second velocity. In an embodiment, the first velocity may be a maximum velocity, a minimum velocity, the velocity indicated by the user, or any other velocity. The second velocity may be any velocity that is detectably different than the first velocity. Thus, if the first velocity is a maximum velocity of the motor, the second velocity may be lower than the first. Conversely, if the first velocity is a low velocity, the second velocity may be higher than the first.

In an embodiment, the lower the battery, the greater than change in speed. In an alternate embodiment, the time between first speed and the change to the second speed may be varied so that less charge means less time before the speed is reduced (or, alternately, more time means less charge). Alternatively, the speed could be changed for just a very short time—in an embodiment, only a few tens of milliseconds, to 'blip' the speed. This would give aural and tactile information to the user. In an embodiment, the number of blips may represent the charge or some other message to the user. For example, more blips may mean less charge. This method could be used independent of the start-up phase, the sequence of blips being repeated every ten seconds, for example.

In an alternate embodiment, or in addition to the method described in connection with FIG. 13, the power supplied to motor 950 may be pulsed in order to cause motor 950 to emit an audible sound. This sound may be modified both in tone, amplitude and duration to produce a series of coded beeps to convey information. Alternately, the sound may be modified to music or pre-recorded spoken messages. This sound may be used to convey battery levels, settings, statuses, etc.

The above-described embodiments of the described subject matter can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single device or computer or distributed among multiple devices/computers.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. A power unit for a motorized surgical tool, comprising:
an outer enclosure defining an interior cavity;
at least one battery cell fully disposed within said interior cavity; and
a printed circuit board disposed within said interior cavity and fully wrapped around said at least one battery cell as a layer of thermal insulation and wherein the printed circuit board is at least partially rigid, wherein the printed circuit board includes rigid panels and flexible portions, and wherein the rigid panels are connected by the flexible portions.

2. The power unit of claim 1, further comprising at least one layer of insulation at least partially wrapped around said at least one battery as a layer of thermal insulation.

3. The power unit of claim 1, wherein the printed circuit board is at least partially formed from a flexible printed circuit board material.

4. The power unit of claim 1, wherein the battery cell is a high-temperature battery.

5. The power unit of claim 1, further comprising a hermetic connector extending from the enclosure, wherein the enclosure and hermetic connector are together hermetically sealed.

6. The power unit of claim 5, wherein the power unit further comprises a bulkhead surrounding the hermetic connector, wherein the bulkhead comprises an O-ring, stretched into a non-circular path, and configured to radially seal a junction between the bulkhead and the enclosure.

7. The power unit of claim 5, wherein the hermetic connector further comprises a plurality of pins.

8. The power unit of claim 7, wherein at least one of the plurality of pins is in communication with the printed circuit board, wherein the printed circuit board is configured to multiplex a first signal and a second signal over the at least one pin of the plurality of pins.

9. The power unit of claim 5, wherein the hermetic connector further comprises a plurality of hyperbolic pin sockets.

10. The power unit of claim 1, wherein the interior cavity of the enclosure is a vacuum.

11. The power unit of claim 10, further comprising a one-way check valve in communication with the interior cavity and an exterior surface of the enclosure, wherein the one-way check valve is configured to refresh the vacuum of the enclosure when the exterior surface of the enclosure is exposed to a vacuum.

12. The power unit of claim 1, wherein said power unit further comprises a canted spring disposed in a channel to secure said power unit to a surgical handpiece motorized unit.

13. The power unit of claim 1, wherein the power unit further comprises a transceiver configured to communicate with a computing device.

14. The power unit of claim 1, wherein the power unit is configured to vary the power delivered to a surgical handpiece motorized unit having a motor, such that the speed of the motor may vary in a predetermined way that is perceptible to a user.

* * * * *